United States Patent [19]

Crounse et al.

[11] 4,111,962

[45] Sep. 5, 1978

[54] CERTAIN SUBSTITUTED 2-PHENYLNAPHTHO[1,2-b]FURANE AND -[2,1-b]FURANE

[75] Inventors: Nathan N. Crounse, Cincinnati, Ohio; Kantilal B. Desai, Highland Heights, Ky.

[73] Assignee: Sterling Drug Inc., New York, N.Y.

[21] Appl. No.: 398,673

[22] Filed: Sep. 19, 1973

Related U.S. Application Data

[63] Continuation-in-part of Ser. No. 118,076, Feb. 23, 1971, Pat. No. 3,781,279.

[51] Int. Cl.$^2$ .......................................... C07D 307/92
[52] U.S. Cl. .............................. 260/346.71; 424/285
[58] Field of Search .................... 260/346.2 M, 346.71

[56] References Cited

U.S. PATENT DOCUMENTS

| | | | |
|---|---|---|---|
| 3,864,333 | 2/1975 | Sahm et al. | 260/346.2 M |
| 3,928,390 | 12/1975 | Sahm et al. | 260/346.2 M |

FOREIGN PATENT DOCUMENTS

| | | |
|---|---|---|
| 2,238,644 | 2/1973 | Fed. Rep. of Germany. |
| 1,224,664 | 3/1971 | United Kingdom. |

*Primary Examiner*—Henry R. Jiles
*Assistant Examiner*—Bernard Dentz
*Attorney, Agent, or Firm*—Thomas L. Johnson; B. Woodrow Wyatt

[57] ABSTRACT

2-Phenylnaphtho[1,2-b]furan, 2-phenylnaphtho[2,1-b]-furan and derivatives thereof substituted in the phenyl ring by alkyl, halo or cyano are useful as antifertility agents, and are prepared by cyclization of a naphthyloxyacetophenone with a strong acid.

7 Claims, No Drawings

CERTAIN SUBSTITUTED 2-PHENYLNAPHTHO[1,2-b]FURANE AND -[2,1-b]FURANE

This application is a continuation-in-part of copending application Ser. No. 118,076, filed Feb. 23, 1971, now U.S. Pat. No. 3,781,279.

This invention relates to compositions and methods for preventing or reducing the incidence of pregnancy in female mammals, to certain novel compounds useful for said purpose and to processes for preparing said compounds.

In prior application Ser. No. 118,076 the compounds 2-(p-tolyl)naphtho[2,1-b]furan and 2-(p-tolyl)naphtho[1,2-b]furan are disclosed as intermediates for the preparation of brightening agents, and they are also disclosed to be useful as antifertility agents in mammalian animals.

It has now been discovered that this property is also present in analogous compounds of the naphthofuran series. Accordingly, one aspect of the invention relates to a composition for preventing or reducing the incidence of pregnancy in female mammals which comprises a contraceptively effective amount of a compound having the formula

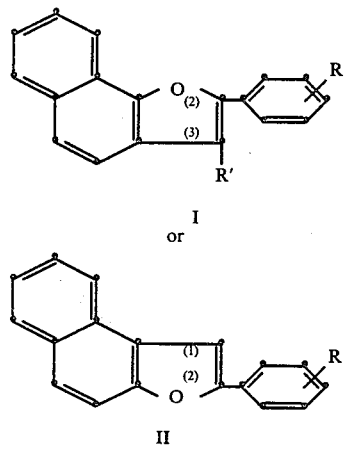

I or

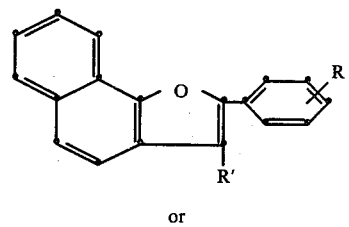

II wherein R is hydrogen, lower-alkyl of 1 to 3 carbon atoms, halo or cyano; and R' is hydrogen, bromo or nitro; incorporated in an inert pharmaceutical carrier.

A further aspect of the invention relates to a method for preventing or reducing the incidence of pregnancy in female mammals which comprises administering to said mammals a contraceptively effective amount of a composition comprising a compound of formulas I or II.

In the foregoing formulas I and II, R thus can be hydrogen, methyl, ethyl, propyl, isopropyl, fluoro, chloro, bromo, iodo, or cyano, and the R group can be in the ortho-, meta-, or para-position with respect to the heterocyclic moiety, although the para-position is preferred.

The compounds of the above formulas I and II where R and R' are hydrogen are known in the art [Thomas and Bokadia, J. Indian Chem. Soc. 43(11), 713 (1966)]. The compounds where R is methyl and R' is hydrogen are also known and disclosed to be useful as intermediates for the preparation of optical brightening agents (British Pat. No. 1,224,664, published Mar. 10, 1971). It has now been found that these compounds as well as the remaining compounds within the scope of formulas I and II, which compounds are new to the art, haver antifertility activity and prevent or reduce the incidence of pregnancy when adminstered to female mammals exposed to mating conditions.

A further aspect of the invention resides in new chemical compounds having the formula

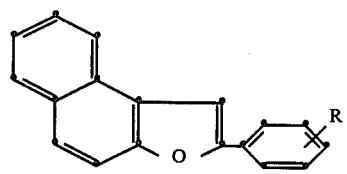

or

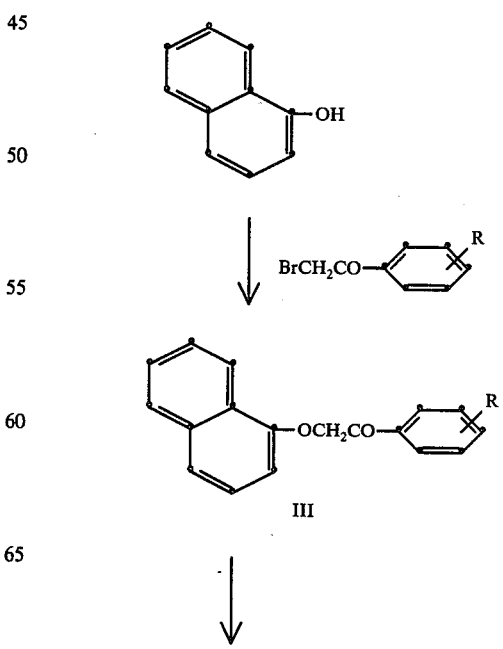

wherein R is halo or cyano, and R' is hydrogen, bromo or nitro. A preferred class of compounds are those where R is p-halo and R' is hydrogen.

The compounds of formula I are prepared by the following reaction sequence starting from α-naphthol:

III

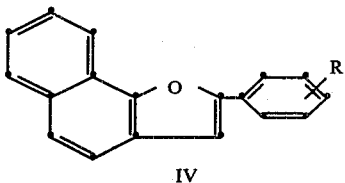

IV

↓

I (R' = H)

α-Naphthol is condensed with a phenacyl bromide, BrCH₂COC₆H₄R, where R is hydrogen, lower-alkyl of 1 to 3 carbon atoms or halo, under alkaline conditions, for example with potassium carbonate in an inert solvent, to produce an α-naphthyloxyacetophenone of formula III. The latter when heated with a strong acid is cyclized to a 3-arylnaphtho[1,2-b]furan of formula IV, which upon further heating with a strong acid is rearranged to a 2-arylnaphtho[1,2-b]furan of formula I.

Any strong acid dehydrating medium can be used to effect the conversion III→IV→I, for example polyphosphoric acid, phosphorus pentoxide, sulfuric acid, lower-alkanesulfonic acids and the like. Polyphosphoric acid is a preferred strong acid dehydrating medium. It is prepared by heating phosphoric acid with sufficient phosphoric anhydride to give the resulting product an 82–85% phosphorus pentoxide content and consists of 55% tripolyphosphoric acid, the remainder being phosphoric acid and other polyphosphoric acids. The cyclization to the 3-arylnaphtho[1,2-b]furans of formula IV takes place at temperatures ranging from about 60° C. to about 100° C. The rearrangement to the 2-arylnaphtho[1,2-b]furans of formula I takes place at temperatures ranging from about 100° C. for the compound where R is hydrogen to temperatures above about 130° C. for compounds where R is other than hydrogen. Temperatures up to about 250° C. can be employed if desired.

Compounds of formula I where R is cyano can be prepared from compounds of formula I where R is halo, preferably chloro, bromo or iodo by replacement of the halo group by cyano, for example by reacting the halo compound with cuprous cyanide.

Compounds of formula I where R' is bromo or nitro can be prepared from the respective compounds of formula I where R' is hydrogen by bromination and nitration procedures, respectively.

The compounds of formula II are prepared by an analogous reaction sequence starting from β-naphthol, viz.:

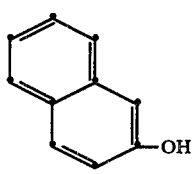

↓

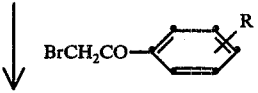

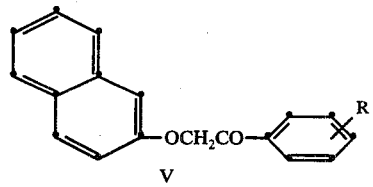

V

↓

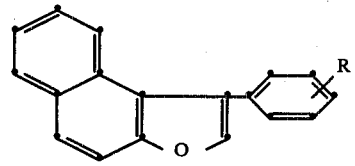

VI

↓

II

An alternative method of preparing compounds of formulas I and II is by cyclization of benzyloxynaphthaldehydes of the formulas:

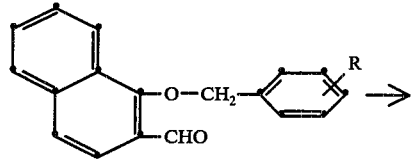

VII or

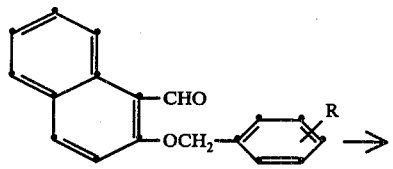

VIII

The cyclization takes place in the presence of a strong base in an inert solvent under anhydrous conditions at ambient temperature. The strong base can be any of the usual aldol condensation reagents, for example, alkali metal lower-alkoxides, hydrides or amides.

The compounds of formulas VII and VIII are prepared by etherification of 1-hydroxy-2-naphthaldehyde or 2-hydroxy-1-naphthaldehyde, respectively, with the appropriate benzyl bromide, BrCH₂C₆H₄R, under alkaline conditions.

Still another method for preparing the compounds of formulas I and II is by reacting 1-iodo-2-hydroxynaphthalene or 1-hydroxy-2-iodonaphthalene with a compound of the formula

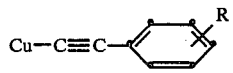

where R is hydrogen, lower-alkyl or halo. The reaction between the iodonaphthol and the copper phenylacetylide takes place at a temperature between about 100° C and 175° C. in an inert solvent. A preferred solvent is pyridine.

The antifertility activity of the compounds of the invention was determined by the following standard test procedure using female rats which were medicated prior to, during and after the mating period. The rats were autopsied on the 14th post mating day and the uteri were examined for evidence of pregnancy. The procedural details are as follows. A colony of sexually mature female rats of the Sprague-Dawley strain weighing 200–300 gms. are maintained on routine laboratory care. Daily vaginal smears are examined to record the cyclic characteristics of each rat. A given test is composed of rats which have exhibited a minimum of 3 coincidental estrus cycles. Three days prior to an expected estrus the rats to be placed on test are grouped, housed individually and placed on medication. The medication consists of a test compound, prepared as a solution or suspension in a suitable vehicle, administered subcutaneously, or orally via stomach tube, once daily for a total of 8 medications in a 10 day period (Sunday medications are omitted). One group receives only the vehicle in a like manner to serve as a control. Late in the afternoon of the day preceding the expected estrus a mature proven fertile male is housed with each female overnight. The following morning all males are removed and a vaginal smear of each female is examined for the presence of spermatozoa as evidence that insemination has occured. Medication of all inseminated rats is continued through the 7th post insemination day. The rats are autopsied 7 days after the last medication and the uteri removed and examined for evidence of pregnancy. The number of implantation sites, number of resorption sites, total number of fetuses and the number of viable fetuses are recorded. When tested by this procedure, the compounds of the invention were found to have antifertility at does levels ranging from about 50 to 200 mg. per kg. per day. All of the compounds of formulas I and II are active subcutaneously and some are also active orally. A particularly preferred group of compounds are those where R is halo, which group possess both subcutaneous and oral activity.

The actual determination of the numerical antifertility data definitive for a particular compound is readily obtained by standard test procedures, referred to above, by technicians versed in endocrinological test procedures, without any need for any extensive experimentation.

The compounds of the invention can be prepared for use by conventional pharmaceutical procedures: that is, by dissolving or suspending them in a pharmaceutically acceptable vehicle, e.g., aqueous alcohol, glycol, oil solution, or oil-water emulsion, for parenteral or oral administration; or by incorporating them in unit dosage form as tablets or capsules for oral administration either alone or in combination with conventional adjuvants, e.g., calcium carbonate, starch, lactose, talc, magnesium stearate, gum acacia, and the like.

The following examples will illustrate the invention without the latter being limited thereby.

EXAMPLE 1

2-(p-Tolyl)naphtho[2,1-b]furan [II; R is p-CH$_3$].

α-(β-Naphthyloxy)-4-methylacetophenone (27.6 g., 0.1 mole) was heated with 250 ml. of polyphosphoric acid and 25 ml. of methanesulfonic acid at 135°–140° C. for eight hours. The reaction mixture was allowed to cool and was then poured into excess water. The resulting precipitate was collected, washed with 10% sodium hydroxide solution, and then washed free of alkali. Crystallized from ethylene glycol, the resulting 2-(p-tolyl)naphtho[2,1-b]furan melted at 145°–147° C.

2-(p-Tolyl)naphtho[2,1-b]furan when tested in female rats according to the procedure described above was found to cause decreased fetuses at 50 mg/kg subcutaneously (s.c.), greatly reduced fetuses at 100 mg/kg s.c., and reduction in viable fetuses at 200 mg/kg orally p.o.).

EXAMPLE 2

2-(p-Tolyl)-naphtho[1,2-b]furan [I; R is p-CH$_3$, R' is H].

α-(α-Naphthyloxy)-4-methylacetophenone (27.6 g.) was heated with 200 ml. of polyphosphoric acid at 135°–140° C. for eight hours. The product was isolated as described in Example 1 crystallized from ethylene glycol to give 2-(p-tolyl)naphtho[1,2-b]furan, m.p. 106°–107° C.

2-(p-Tolyl)naphtho[1,2-b]furan when tested in female rats according to the procedure described above was found to cause greatly reduced fetuses at 50 and 100 mg/kg s.c.

EXAMPLE 3

α-(α-Naphthyloxy)-4-bromoacetophenone [III; R is 4-Br].

A mixture of 43.25 g. (0.30 mole) of α-naphthol, 45.61 g. (0.33 mole) of potassium carbonate, 83.39 g. (0.30 mole) of α,p-dibromoacetophenone and 450 ml. of acetone was stirred under reflux for 19 hours. The reaction mixture was filtered and the filtrate evaporated to remove the solvent. The residue was dissolved in chloroform and the chloroform solution washed with dilute sodium hydroxide solution and concentrated to dryness. The product was recrystallized from isopropyl alcohol and dried at 60° C. in vacuo for 18 hours to give 84.68 g. of α-(α-naphthyloxy)-4-bromoacetophenone, m.p. 90°–91° C. (light tan prisms).

(b) 2-(p-Bromophenyl)naphtho[1,2-b]furan [I; R is p-Br, R' is H].

A mixture of 84.57 g. (0.248 mole) of α-(α-naphthyloxy)-4-bromoacetophenone and 500 ml. of polyphosphoric acid was stirred and heated at 203±3° C. for four and one-half hours. The mixture was added to water, and the solid product was collected by filtration, recrystallized from acetonitrile, using activated charcoal for decolorizing purposes, and dried in vacuo at 60° for 18 hours, to give 53.89 g. of 2-(p-bromophenyl)-naphtho[1,2-b]furan, m.p. 120°–134° C. Further recrystallization gave a sample with m.p. 136°–137° C. (light tan prisms).

2-(p-Bromophenyl)naphtho[1,2-b]furan when tested in female rats according to the procedure described above was found completely effective at 200 mg/kg s.c.

(no fetuses) and p.o. and caused reduced fetuses at 100 mg/kg p.o.

EXAMPLE 4

2-Phenylnaphtho[2,1-b]furan [II; R is H] was prepared from 96.4 g. of α-(β-naphthyloxy)acetophenone (m.p. 95°–99° C.) and 450 ml. of polyphosphoric acid, five hours at 100±2° C. There was obtained 42.3 g. of 2-phenylnaphtho[2,1-b]furan, light tan solid, m.p. 140.5°–144° C. (from methanol).

2-Phenylnaphtho[2,1-b]furan when tested in female rats according to the procedure described above was found completely effective at 200 mg/kg s.c. (no fetuses).

EXAMPLE 5

2-Phenylnaphtho[1,2-b]furan [I; R and R' are H] was prepared from 114.4 g. of α-(α-naphthyloxy)acetophenone (tan prisms, m.p. 68°–69° C.) and 600 ml. of polyphosphoric acid, 4.5 hours at 105±4° C. There was obtained 45.10 g. of 2-phenylnaphtho[1,2-b]furan, tan prisms, m.p. 109.5°–111° C. (from ethanol).

2-Phenylnaphtho[1,2-b]furan when tested in female rats according to the procedure described above was found to cause greatly reduced fetuses at 200 mg/kg s.c.

EXAMPLE 6

2-(p-Bromophenyl)naphtho[2,1-b]furan [II; R is p-Br] was prepared from 20.0 g. of α-(β-naphthyloxy)-4-bromoacetophenone (light tan prisms, m.p. 120°–121° C.) and 85 ml. of polyphosphoric acid, 3.5 hours at 202±3° C. There was obtained 10.14 g. of 2-(p-bromophenyl)naphtho[2,1-b]furan, tan prisms, m.p. 158°–159.5° C. (from acetonitrile).

2-(p-Bromophenyl)naphtho[2,1-b]furan when tested in female rats according to the procedure described above was found completely effective at 200 mg/kg s.c. (no fetuses) and caused decreased fetuses at 200 mg/kg p.o.

EXAMPLE 7

2-(p-Chlorophenyl)naptho[2,1-b]furan [II; R is p-Cl] was prepared from 25.0 g. of α-(β-naphthyloxy)-4-chloroacetophenone (light yellow-tan prisms, m.p. 107.5°–108.5° C.) and 225 ml. of polyphosphoric acid, 5.5 hours at 203±5° C. There was obtained 17.1 g. of 2-(p-chlorophenyl)naphtho[2,1-b]furan, tan solid, m.p. 153.5°–155° C. (from acetonitrile).

2-(p-Chlorophenyl)naphtho[2,1-b]furan when tested in female rats according to the procedure described above was found completely effective at 200 mg/kg s.c. (no fetuses) and was active at 250 mg/kg p.o.

According to the procedures given in the preceding examples α-(α-naphthyloxy)-4-chloroacetophenone, α-(α-napthyloxy)-4-fluoroacetophenone, α-(α-naphthyloxy)-4-iodoacetophenone, α-(β-naphthyloxy)-4-fluoroacetophenone, α-(β-naphthyloxy)-4-iodoacetophenone, α-(β-naphthyloxy)-2-bromoacetophenone, or α-(β-naphthyloxy)-3-bromoacetophenone can be cyclized with polyphosphoric acid at temperatures above about 130° C. to give, respectively, 2-(p-chlorophenyl)naphtho[1,2-b]furan [I; R is p-Cl, R' is H], 2-(p-fluorophenyl)naphtho[1,2-b]furan [I; R is p-F, R' is H], 2-(p-iodophenyl)naphtho[1,2-b]furan [I; R is p-I, R' is H], 2-(p-fluorophenyl)naphtho[2,1-b]furan [II; R is p-F], 2-(p-iodophenyl)naphtho[2,1-b]furan [II; R is p-I], 2-(o-bromophenyl)naphtho[2,1-b]furan [II; R is o-Br]a or 2-(m-bromophenyl)naphtho[2,1-b]furan [II; R is m-Br].

Similarly, α-(β-naphthyloxy)-4-propylacetophenone or α-(β-naphthyloxy)-4-isopropylacetophenone can be cyclized to give, respectively, 2-(p-propylphenyl)naphtho[2,1-b]furan [II; R is p-CH₃CH₂CH₂], or 2-(p-isopropylphenyl)naphtho[2,1-b]furan [II; R is p-(CH₃)₂CH].

EXAMPLE 8

2-(p-Cyanophenyl)naphtho[2,1-b]furan [II R is p-CN].

A mixture of 16.16 g. (0.050 mole) of 2-(p-bromophenyl)naphtho[2,1-b]furan (Example 6), 10.6 g. (0.06 mole) of cuprous cyanide and 250 ml. of N-methylpyrrolidone was stirred and heated at 190°–203° C. for 4.5 hours. The mixture was then poured into 500 ml. of water to which had been added 40 g. of ferric chloride hexahydrate and 100 ml. of concentrated hydrochloric acid. The mixture was stirred 5–10 minutes and water was then added until precipitation of solid was complete. The solid product was collected, recrystallized from isopropyl alcohol and chromatographed on 400 g. of silica gel, applied in ether. The chromatograph column was eluted with an equal volume mixture of hexane and ether to give 5 g. of 2-(p-cyanopyenyl)naphtho[2,1-b]furan, pale yellow prisms, m.p. 165°–166° C. after recrystallization from isopropyl alcohol.

2-(p-Cyanophenyl)naptho[2,1-b]furan when tested in female rats according to the procedure described above was found to cause decreased fetuses at 200 mg/kg s.c.

Similarly, 2-(p-bromophenyl)napho[1,2-b]furan (Example 3b) can be converted to 2-(p-cyanophenyl)naphtho[1,2-b]furan [I; R is p-CN, R' is H].

EXAMPLE 9

(a) 2-(p-Cyanobenzyloxy)-1-naphthaldehyde [VIII; R is p-CN].

2-Hydroxy-1-naphthaldehyde (34.44 g., 0.20 mole) was added to a solution of 13.04 g. (0.20 mole) of potassium hydroxide in 800 ml. of absolute ethanol and the mixture stirred for 45 minutes. To the resulting solution of the potassium salt of the phenol aldehyde was added 43.13 g. (0.22 mole) of α-bromo-p-tolunitrile, and the mixture was stirred under reflux for 23 hours. The reaction mixture was cooled, and the solid material was collected by filtration, washed with water and recrystallized from acetonitrile to give 35.64 g. of 2-(p-cyanobenzyloxy)-1-naphthaldehyde, tan prisms, m.p. 163°–164° C.

(b) 2-(p-Cyanophenyl)naphtho[2,1-b]furan [II R is p-CN].

A mixture of 41.3 g. (0.144 mole) of 2-(p-cyanobenzyloxy)-1-naphthaldehyde and 1.56 g. (0.0288 mole) of sodium methoxide in 600 ml. of dimethylformamide was stirred at room temperature for 160 minutes. The reaction mixture was poured into water, and the solid material was collected by filtration, washed with water, recrystallized from isopropyl alcohol and dried at 60° in vacuo for 18 hours to give 24.52 g. of 2-(p-cyanophenyl)-naphtho[2,1-b]furan, m.p. 166.5°–168° C., identical with the compound obtained in Example 8.

By replacing the 2-hydroxy-1-naphthaldehyde in the foregoing example by 1-hydroxy-2-naphthaldehyde, there can be obtained 2-(p-cyanophenyl)naphtho[1,2-b]furan [I; R is p-CN, R' is H].

EXAMPLE 10

3-Bromo-2-(p-bromophenyl)naphtho[1,2-b]furan [I; R is p-Br, R' is Br].

A solution (58.5 ml., 0.03 mole) of bromine in acetic acid (0.513 mole per liter) was added over a period of 90 minutes to a stirred suspension of 9.70 g. (0.03 mole) of 2-(p-bromophenyl)naphtho[1,2-b]furan (Example 3b) at 60° C. The mixture was stirred for 30 minutes longer, and the solid material was collected by filtration, washed with water, recrystallized from acetonitrile and dried at 60° in vacuo for 20 hours to give 9.03 g. of 3-bromo-2-(p-bromophenyl)naphtho[1,2-b]furan, light tan prisms, m.p. 162°–162.5° C.

3-Bromo-2-(p-bromophenyl)naphtho[1,2-b]furan when tested in female rats according to the procedure described above was found to cause decreased fetuses at 200 mg/kg s.c.

Similarly, 2-(p-tolyl)naptho[1,2-b]furan (Example 2), 2-phenylnaphtho[1,2-b]furan (Example 5), 2-(p-cyanophenyl)naphtho[1,2-b]furan, or 2-(p-chlorophenyl)naphtho[1,2-b]furan can be brominated to produce, respectively, 3-bromo-2-(p-tolyl)naphtho[1,2-b]furan [I; R is p-CH₃, R' is Br],
3-bromo-2-phenylnaphtho[1,2-b]furan [I; R is H, R' is Br],
3-bromo-2-(p-cyanophenyl)naphtho[1,2-b]furan [I; R is p-CN, R' is Br], or
3-bromo-2-(p-chlorophenyl)naphtho[1,2-b]furan [I; R is p-Cl, R' is Br].

EXAMPLE 11

2-(p-Bromophenyl)-3-nitronaphtho[1,2-b]furan [I; R is p-Br, R' is NO₂].

A solution of 1.8 ml. (0.038 mole) of 90% nitric acid in 15-20 ml. of acetic acid was added dropwise to a stirred suspension of 8.79 g. (0.271 mole) of 2-(p-bromophenyl)naphtho[1,2-b]furan (Example 3b) with intermittent warming over a period of 40 minutes. The reaction mixture was stirred for 90 minutes at 40°–50° C., allowed to stand at room temperature for 16 hours, stirred at 40°–50° C. for 150 minutes and then at 60° C. for 30 minutes. The mixture was cooled and filtered into 500 ml. of water with stirring. The solid product was collected by filtration and recrystallized from acetonitrile to give 5.1 g. of 2-(p-bromophenyl)-3-nitronaphtho[1,2-b]furan, light yellow needles, m.p. 200°–201° C.

2-(p-Bromophenyl)-3-nitronaphtho[1,2-b]furan when tested in female rats according to the procedure described above was found to cause decreased fetuses at 200 mg/kg s.c.

Similarly, 2-(p-tolyl)naphtho[1,2-b]furan (Example 2), 2-phenylnaphtho[1,2-b]furan (Example 5), 2-(p-cyanophenyl)naphtho[1,2-b]furan, or 2-(p-chlorophenyl)naphtho[1,2-b]furan can be nitrated to produce, respectively, 3-nitro-2-(p-tolyl)naphtho[1,2-b]furan [I; R is p-CH₃, R' is NO₂],
3-nitro-2-phenylnaphtho[1,2-b]furan [I; R is H, R' is NO₂],
2-(p-cyanophenyl)-3-nitronaphtho[1,2-b]furan [I; R is p-CN, R' is NO₂], or
2-(p-chlorophenyl)-3-nitronaphtho[1,2-b]furan [I; R is p-Cl, R' is NO₂).

We claim:
1. A compound of the formula

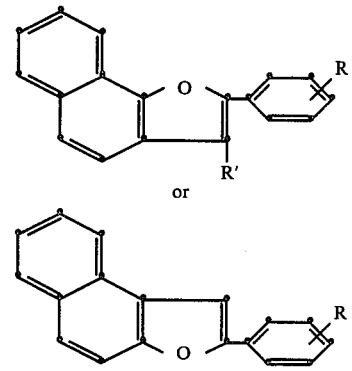

wherein R is halo and R' is hydrogen, bromo or nitro.

2. A compound according to claim 1 wherein R is p-halo and R' is hydrogen.

3. 2-(p-Bromophenyl)naphtho[1,2-b]furan, according to claim 2.

4. 2-(p-Bromophenyl)naphtho[2,1-b]furan, according to claim 2.

5. 2-(p-Chlorophenyl)naphtho[2,1-b]furan, according to claim 2.

6. 3-Bromo-2-(p-bromophenyl)naphtho[1,2-b]furan, according to claim 1.

7. 2-(p-Bromophenyl)-3-nitronaphtho[1,2-b]furan, according to claim 1.

* * * * *

UNITED STATES PATENT AND TRADEMARK OFFICE
CERTIFICATE OF CORRECTION

PATENT NO. : 4,111,962
DATED : September 5, 1978
INVENTOR(S) : Nathan N. Crounse & Kantilal B. Desai It is certified that error appears in the above—identified patent and that said Letters Patent are hereby corrected as shown below:

Cover page and column 1, in title, "FURANE", each occurrence, should read --FURANS--.

Column 3, formula IV,

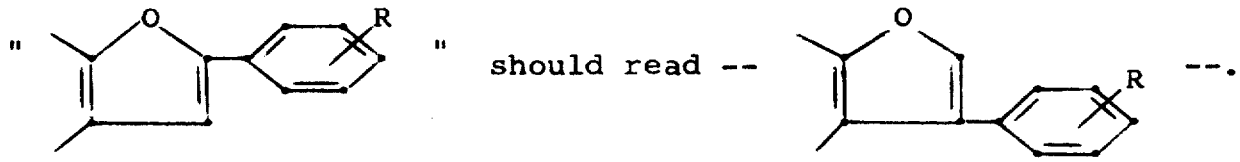

Column 5, line 46, "does" should read --dose--.

Column 7, line 42, "naptho" should read --naphtho--; line 55, "napthyloxy" should read --naphthyloxy--.

Column 8, line 3, "o-Br]a" should read --o-Br],--; line 30, "cyanopyenyl" should read --cyanophenyl--.

Column 9, line 43, "0.271 mole" should read --0.0271 mole--.

Signed and Sealed this

Seventeenth Day of April 1979

[SEAL]

Attest:

RUTH C. MASON
Attesting Officer

DONALD W. BANNER
Commissioner of Patents and Trademarks